United States Patent [19]
Ito et al.

[11] Patent Number: 5,243,368
[45] Date of Patent: Sep. 7, 1993

[54] OPHTHALMOLOGIC APPARATUS

[75] Inventors: Kosuke Ito, Toyohashi; Chikashi Koike, Hino; Hirokatsu Nakano, Gamagouri, all of Japan

[73] Assignee: Kowa Company Ltd., Japan

[21] Appl. No.: 597,444

[22] Filed: Oct. 15, 1990

[30] Foreign Application Priority Data
Oct. 16, 1989 [JP] Japan .................. 1-266247

[51] Int. Cl.$^5$ ................................. A61B 3/10
[52] U.S. Cl. .................... 351/221; 351/212; 351/214
[58] Field of Search ............... 351/221, 212, 214, 208; 606/4, 5

[56] References Cited
U.S. PATENT DOCUMENTS
3,703,176 11/1972 Vassiliadis et al. ............... 606/4

Primary Examiner—Rodney B. Bovernick
Assistant Examiner—Hung Xuan Dang
Attorney, Agent, or Firm—Bruce L. Adams; Van C. Wilks

[57] ABSTRACT

An ophthalmologic apparatus equipped with a projection optical system for projecting a laser beam spot image onto a prescribed point of an eye under examination has a zoom lens provided in the projection optical system for enabling the diameter of the projected spot image to be varied and some of the lenses of the zoom lens are made movable for enabling projection of a blurred spot image.

5 Claims, 3 Drawing Sheets

OPHTHALMOLOGIC APPARATUS

BACKGROUND OF THE INVENTION

1. Field of the Invention

This invention relates to an ophthalmologic apparatus, and more particularly to an ophthalmologic apparatus having a projection optical system for projecting a laser beam onto a prescribed point of an eye under examination as a spot image.

2. Description of the Prior Art

Ophthalmologic apparatuses of this type include, for example, the laser beam coagulation apparatus which is used for directing a laser beam onto living tissue within the eye for raising the tissue to a high temperature and causing it to thermocoagulate. In using this apparatus, it is necessary to adjust the diameter of the laser beam spot according to the size of the portion to be subject to thermocoagulation. Conventionally, a zoom lens optical system has been used for this adjustment of the spot diameter.

The zoom lens optical system used in such an ophthalmologic apparatus comprises first and second lens groups which can be moved with respect to each other to provide variable power capability. Since the lens groups are moved so that the surface from which the laser beam is emitted and the point at which the spot image is formed fall at the conjugate points of the zoom lens optical system, it is consistently possible to obtain a spot image that is in good focus and has a sharp edge.

In the case of conducting laser beam coagulation, however, it is not always desirable to use a sharp-edged image and there are cases in which it is better to conduct the optical coagulation with a spot image having a fuzzy edge. For this, it is necessary to form the spot image at a position that is not at the focal point so as to separate it from the conjugate position. Where a zoom lens is used to realize variable power capability, however, the aforesaid movement of the lens groups is controlled so as to maintain the conjugate relationship. Thus the spot image is always in focus and it is not possible to obtain a spot image with a fuzzy edge.

SUMMARY OF THE INVENTION

An object of the present invention is, therefore to provide an ophthalmologic apparatus of simple structure which is able to vary the size of a laser beam spot image and to provide a spot image with a fuzzy edge.

For realizing this object, the present invention provides an ophthalmologic apparatus having a projection optical system for projecting a laser beam onto a prescribed point of an eye under examination as a spot image, wherein the projection optical system comprises a zoom lens for varying the diameter of the spot image and some of the lenses constituting the zoom lens are movable for enabling projection of a spot image with a fuzzy edge.

With this arrangement, since the projection optical system for the laser beam includes a zoom lens, the size of the projected spot image can be varied. Moreover, since some of the lenses constituting the zoom lens are movable, it is possible to project a spot image that is out of focus and has a fuzzy edge. Preferably the movement of the lenses constituting the zoom lens should be controlled by cam grooves provided in the zoom lens-barrel so as to enable either variable power projection of a sharp-edged spot image or of a fuzzy-edged spot.

BRIEF DESCRIPTION OF THE DRAWINGS

The objects and features of the present invention will become more apparent from the following detailed description taken in conjunction with the accompanying drawings, in which.

DETAILED DESCRIPTION OF THE PREFERRED EMBODIMENT

Figure 1:
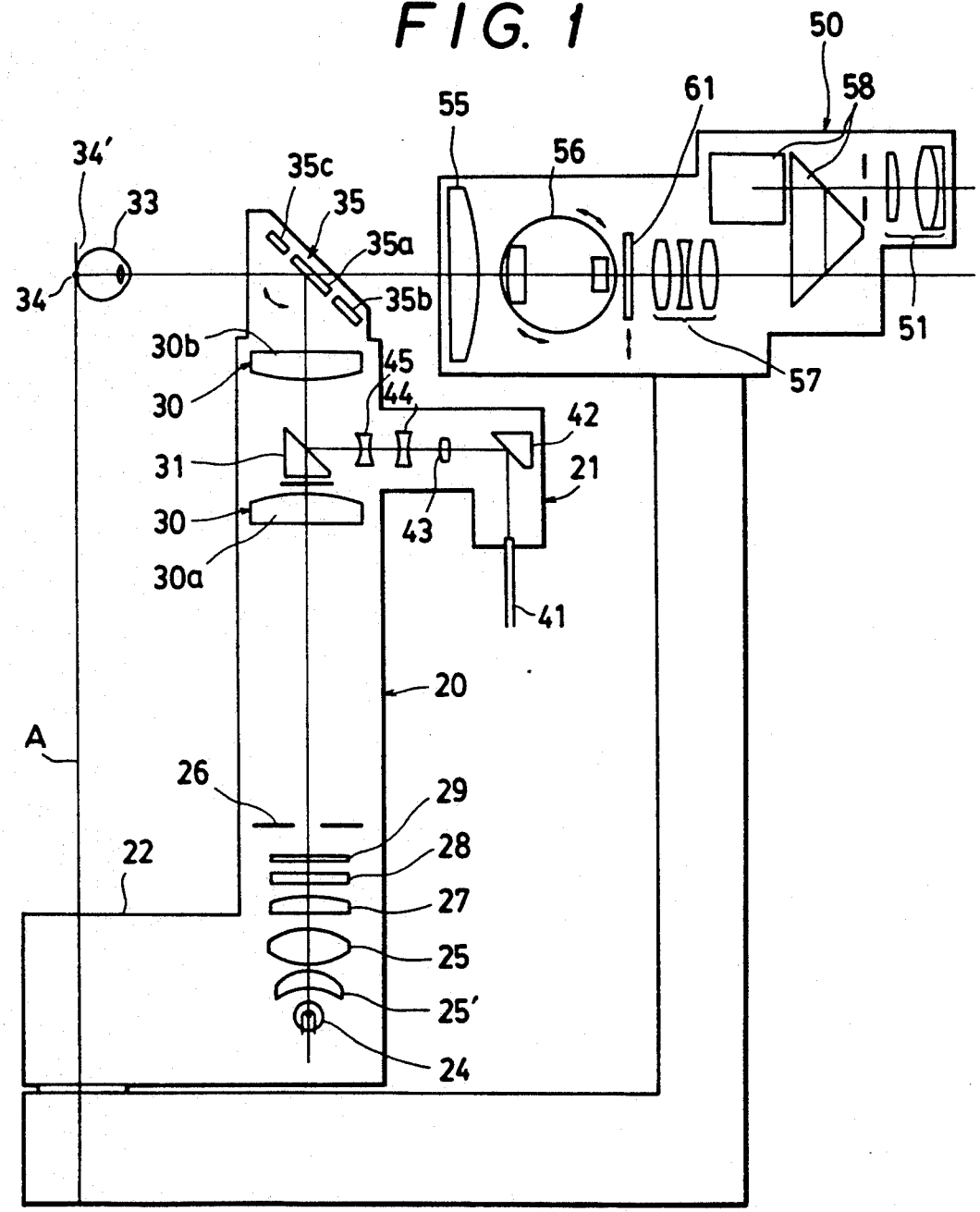
FIG. 1 is a schematic view showing the overall structure of an embodiment of the ophthalmologic apparatus according to this invention.

The invention will now be explained in detail with reference to the embodiment illustrated in the drawings.

FIG. 1 shows an embodiment of the invention as applied to a laser beam coagulation apparatus. The apparatus comprises a laser beam projection optical system 21, a slit image formation optical system 20 and an observation optical system 50. The slit image formation optical system 20 is disposed in a cylindrical member 22 so as to be rotatable about its axis A. Light emitted by a lamp 24 is condensed by condenser lenses 25, 25' and directed onto a slit 26. Between the condenser lens 25 and the slit 26 are disposed a roof deflection prism 27, a heat cut filter 28 and a removable blue filter 29. An image 34' of the illuminated slit 26 is formed at an image focal point 34, located, for example, on the retina of an eye 33 of a patient under examination, by an imaging lens 30 constituted of lenses 30a, 30b. A mirror 35 is disposed between the lens 30b and the eye 33 of the patient. The mirror 35 is constituted of three mirror sections 35a to 35c. Among these mirrors, the center one, mirror 35a, is arranged to be rotatable up and down about an axis perpendicular to the drawing sheet and to be rotatable to the left and right about a horizontal axis within the drawing sheet.

The laser beam projection optical system 21 is disposed within the same cylindrical member 22 as houses the slit image formation optical system 20. A laser beam introduced through an optical fiber 41 is deflected 90° by a mirror 42, passed through a lens 43 and a zoom lens constituted of lenses 44, 45 and reflected by a mirror 31 so as to advance along the same optical axis as that of the slit image formation optical system 20, whereafter it passes through the lens 30 and is reflected by the mirror section 35a to form a spot image 34 on the retina of the eye 33 and coagulate the tissue at this point. The diameter of the laser spot can be varied between approximately 50 micrometers and 1 mm by movement of the zoom lenses 44, 45.

The observation optical system 50 is constituted of an object lens 55, a variable power lens 56, a safety filter 61, an imaging lens 57, erect prisms 58, and an eyepiece 51. The operator is able to observe both the slit image and the laser spot image formed within the eye 33 through the observation optical system 50.

Figure 2:
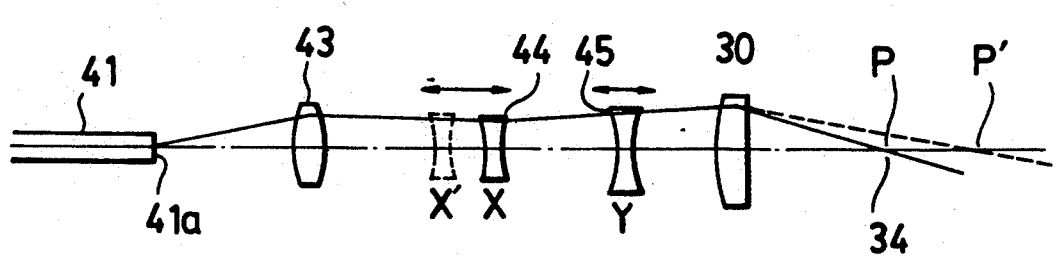
FIG. 2 is an optical diagram showing the arrangement of the lenses of an optical system constituted mainly of a zoom lens system.

FIG. 2 schematically illustrates the portion of the optical system centering on the zoom lenses 44, 45 housed within cylindrical member 22 for the laser beam projection optical system 21. The lenses or lens groups 44, 45, which together constitute a zoom lens and may themselves each be constituted of a plurality of lenses, are disposed so as to be movable along the optical axis in accordance with the curves shown in FIGS. 3 and 4.

Figure 3:
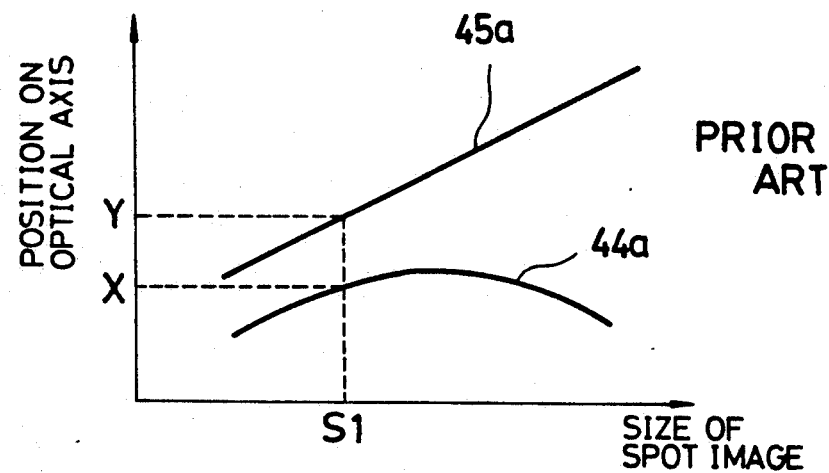
FIG. 3 is a graph showing the relationship between the movement of an ordinary zoom lens system and the size of a spot image.

When the zoom lens operates in the manner of an ordinary zoom lens, the lens 44 moves in the manner indicated by curve 44a in FIG. 3, while the lens 45 moves in the manner indicated by the curve 45a in the same figure. In view of the characteristics shown in FIG. 3, the size of the spot image 34 at the point P becomes S1 when the lenses 44, 45 are at the positions X and Y in FIG. 2. A well-focused, sharp-edged image 34 is consistently obtained at the spot P irrespective of the positions of the lenses 44 since the point P is always at the image focal point having the end surface 41a of the optical fiber 41 as its object focal point, i.e., since the end surface 41a and the point P are the conjugate points. The size of the spot image 34 at this time is determined by which positional relationship shown in FIG. 3 the lenses 44, 45 assume.

Figure 4:
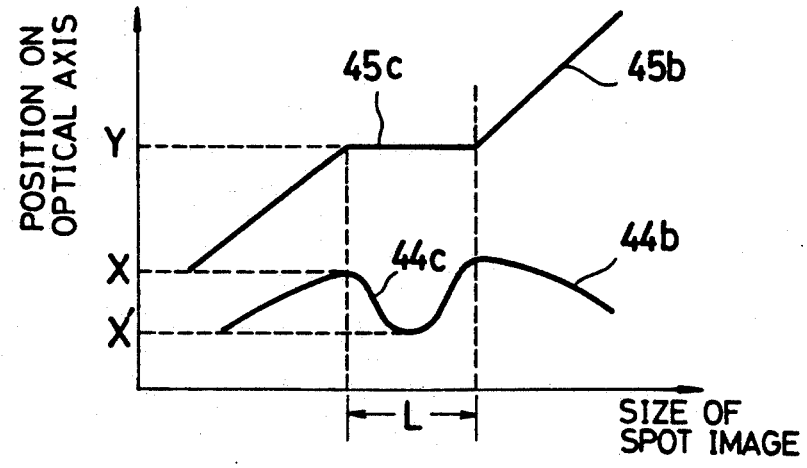
FIG. 4 is a graph showing the relationship between the movement of a zoom lens system according to an embodiment of this invention and the size of a spot image.

So as to enable this embodiment of the invention to produce not only a spot image that is always in sharp focus but also a blurred or fuzzy spot image that is out of focus, the lens 45 is stopped when it is in the position Y, as is shown by curve 45c in FIG. 4. As shown by curve 44c in FIG. 4, the lens 44 is at this time moved between X and X' i.e., moved sequentially away from and then toward the lens 45. As a result, the spot image 34 is not formed at the point P but at the point P'. Therefore, the spot image appearing at point P is blurred and its edge is fuzzy. The length of the zone over which a blurred spot image is formed is indicated by L.

In all other zones, since the lenses 44, 45 move along curves 44b, 45b similar to the curves 44a, 44b of FIG. 3, the spot image 34 is formed at the point P, whereby there is obtained a sharp spot 34 of variable magnification.

Figure 5:
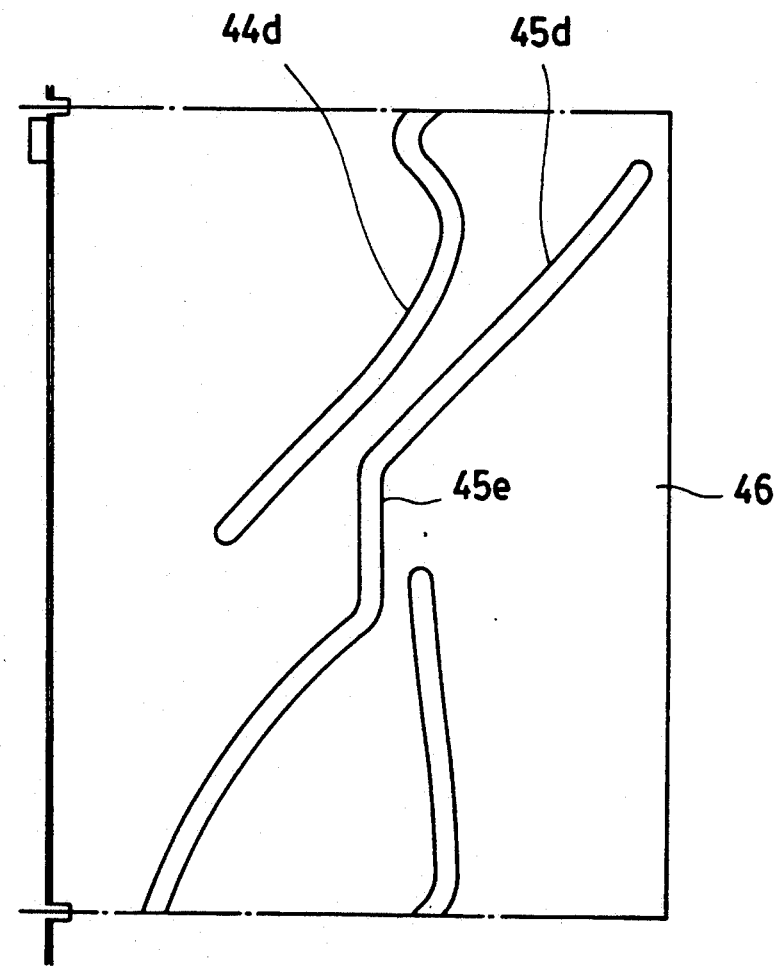
FIG. 5 is a spreaded view of the configuration of cam grooves formed in a zoom lens barrel.

The configuration of cam grooves provided in a rotatable zoom lens barrel 46 for realizing the aforesaid lens movement is shown in FIG. 5. Specifically, the lens 44 moves along the optical axis of the zoom lens in accordance with a cam groove 44d, while the lens 45 moves along the potical axis in accordance with a cam groove 45d. The configuration of the cam groove for keeping the lens 45 stopped or immovable along the optical axis at Y is indicated by reference symbol 45e.

As explained in the foregoing, the ophthalmologic apparatus according to the present invention is provided in its laser beam projection optical system with a zoom lens which enables the size of the projected spot image to be varied. Moreover, since some of the lenses constituting the zoom lens are made movable, it becomes possible to project an out-of-focus, fuzzy-edged spot image using an apparatus of simple arrangement.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmologic apparatus having a projection optical system for projecting a laser beam onto a prescribed point of an eye under examination as a spot image, comprising a zoom lens provided in the projection optical system for enabling the diameter of the projected spot image to be varied, at least one lens of the zoom lens being movable for enabling projection of a blurred spot image.

2. An ophthalmologic apparatus according to claim 1, wherein the zoom lens comprises a plurality of lenses at least one of which is movable and the remainder of which are fixed.

3. An ophthalmologic apparatus according to claim 2, wherein movement of the lenses constituting the zoom lens is controlled by cam grooves provided in a zoom lens barrel.

4. An ophthalmologic apparatus according to claim 1, wherein the zoom lens has a zoom range within which the diameter of the projected spot image can be varied, the blurred spot image being projected within a part of the zoom range.

5. An ophthalmologic apparatus according to claim 4, wherein the zoom lens projects a focused spot image within the whole zoom range except for a limited range within which the blurred spot image is projected.

* * * * *